(12) United States Patent
Luo

(10) Patent No.: US 12,186,485 B1
(45) Date of Patent: Jan. 7, 2025

(54) PATIENT INTERFACE CUSHION WITH FABRIC

(71) Applicant: DCSTAR INC., New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 18/509,932

(22) Filed: Nov. 15, 2023

(51) Int. Cl.
*A61M 16/06* (2006.01)

(52) U.S. Cl.
CPC ................ *A61M 16/0616* (2014.02)

(58) Field of Classification Search
CPC ..... A41D 15/04; A47G 9/086; A61M 16/024; A61M 16/06; A61M 16/0605; A61M 16/0611; A61M 16/0616; A61M 16/0622; A61M 16/0633; A61M 16/0666; A61M 16/0683; A61M 16/0688; A61M 16/0694; A61M 16/0816; A61M 16/0825; A61M 16/0858; A61M 16/0875; A61M 16/1055; A61M 16/107; A61M 16/1075; A61M 16/16; A61M 16/161; A61M 16/208; A61M 16/209; A61M 2016/0027; A61M 2016/0036; A61M 2016/0661; A61M 2202/0007; A61M 2202/0085; A61M 2202/0208; A61M 2202/0225; A61M 2205/02; A61M 2205/0216; A61M 2205/0222; A61M 2205/0238; A61M 2205/276; A61M 2205/3368; A61M 2205/583; A61M 2205/59; A61M 2207/00; A61M 2207/10; A61M 2209/02; A61M 2209/06; A61M 2210/0618; A61M 2210/0625; A62B 18/025; A62B 18/084; B33Y 80/00; Y10S 2/909
See application file for complete search history.

(56) References Cited

U.S. PATENT DOCUMENTS

| | | | | |
|---|---|---|---|---|
| 4,843,647 A | * | 7/1989 | Phillips, Sr | A47G 9/086 2/93 |
| 2006/0207600 A1 | * | 9/2006 | Burrow | A61M 16/0683 128/207.11 |
| 2010/0000534 A1 | * | 1/2010 | Kooij | A61M 16/0616 128/207.13 |
| 2011/0146684 A1 | * | 6/2011 | Wells | A61M 16/06 128/205.25 |
| 2017/0326320 A1 | * | 11/2017 | Baigent | A61M 16/0616 |
| 2022/0096769 A1 | * | 3/2022 | Guney | A61M 16/0611 |
| 2022/0280740 A1 | * | 9/2022 | Scheiner | A61M 16/06 |

* cited by examiner

*Primary Examiner* — Annette Dixon
(74) *Attorney, Agent, or Firm* — HSML P.C.

(57) ABSTRACT

A patient interface cushion and specifically a patient interface cushion with fabric, configured to supply pressurized breathing gas to the nasal and oral airways of a user. The patient interface cushion includes a rigid part, configured to support the elastic part, featuring a first opening and a second opening; The elastic part, configured to provide an attachment surface for the fabric part, featuring a third opening in communication with the second opening and a fourth opening allowing the user's nose and mouth to enter the internal cavity of the elastic part. The fabric part, configured to form a sealing area between the lower lip area and the nasal bridge area, featuring a first surface partially connected to the elastic part, a second surface sealing at least a portion of the user's face, and also having an inner edge and an outer edge.

20 Claims, 15 Drawing Sheets

PATIENT INTERFACE CUSHION WITH FABRIC

TECHNICAL FIELD

This disclosure relates to the field of patient interface cushions, specifically to a cushion for a continuous positive airway pressure therapy device that provides a seal for the user's nasal and oral airways. More specifically, it concerns a patient interface cushion for a continuous positive airway pressure therapy device that has fabric contacting the user's face to improve comfort during wear.

BACKGROUND

To accommodate the different needs and preferences of users, continuous positive airway pressure (CPAP) therapy devices have developed various types and styles of patient interface cushions, such as full-face masks, nasal masks, and nasal pillow masks. Nasal masks and nasal pillow masks are relatively lighter compared to full-face masks, but for users who breathe through their mouths, full-face masks remain the best choice. Recently, new types of oral-nasal masks have appeared on the market that can also provide pressurized gas to the user's oral and nasal airways. However, these types of masks seal the area between the tip of the user's nose, below the nasal bridge, and the lower lip. The seal on the tip of the nose is achieved solely by the pressure of the air inflating the mask against the skin of the nose. In this situation, if the user moves during sleep or if there is individual variability in nose shape, the oral-nasal mask may not fit well. Full-face masks offer better sealing performance and a larger surface area to distribute the pressure.

However, most of the current full-face masks use flexible sealing elements, such as silicone or rubber, to seal against the user's face. These flexible sealing elements are good at conforming to the varying contours of the face. To achieve a good seal, polishing techniques are often employed to reduce the surface roughness of the sealing elements, making them smoother. However, this smooth surface, when in contact with the face, can feel slightly sticky. Moreover, most users wear these masks during sleep at night, with continuous wear time ranging from approximately 6-8 hours or more. During sleep, the face secretes oils and sweat. When these secretions come into contact with the smooth sealing elements, users may feel a sense of stickiness and discomfort, and the secretions may also make the mask more prone to shifting. Long periods of wear, coupled with the tension from the head straps to keep the mask tightly fitted against the skin, can lead to skin irritation and pressure sores. This is especially true for areas on both sides of the nasal bridge where the contours are more pronounced. These areas usually require greater force to tighten the mask, which can result in red marks.

As a result, some products have been introduced to the market to improve user comfort, such as CPAP Mask Liners and CPAP Mask Covers. Mask liners are textile cushions placed between the mask and the user's face to absorb oils and sweat for a more comfortable user experience. However, due to the lack of secure attachment, it is extremely difficult for users to keep the liner in the proper position. Even if it is initially secured, the liner is prone to slipping off due to movement during sleep. Mask covers serve a similar purpose but include an additional feature-a stretchable strap to prevent them from falling off the mask during sleep. However, the side that adheres to the face is still susceptible to movement. Additionally, mask covers tend to be relatively thick; when worn by the user, they may create wrinkles that lead to air leaks. Neither of these solutions effectively address the comfort issues associated with wearing the mask.

A newly released full-face mask featuring a sponge layer has recently come onto the market. This mask helps to alleviate the pressure on the face, reducing the occurrence of red marks and pressure sores. However, the requirements for the sponge are quite high; it needs to have the correct contour shape and the material for the sponge needs to have a permeability that falls within the therapeutic range. Additionally, due to the added sponge layer, the mask is not washable, making it difficult to clean the sponge. When it becomes dirty, it cannot be replaced. The soft sponge is also prone to damage, and if it gets damaged, the entire mask needs to be replaced. Therefore, there is a need to create a mask that offers a better user experience, improves the effectiveness of the treatment, and enhances user compliance.

SUMMARY

Given the above shortcomings, there is a need to provide a patient interface cushion that is easier to clean, replaceable, and more comfortable.

To address these issues, in an embodiment, a patient interface cushion with fabric, designed to deliver pressurized breathing gas to a user's nasal and oral airways is provided. The patient interface cushion includes a rigid part configured to provide support to an elastic part, one end of the rigid part having a first opening designed to receive breathing gas from a CPAP device, and the other end featuring a second opening that communicates with an inner cavity of the elastic part; an elastic part configured to connect with the rigid part and provide an attachment surface for the fabric part, having a third opening adjacent to the rigid part that communicates with the second opening, and a fourth opening away from the rigid part configured to allow the user's mouth and the user's nose to enter the inner cavity of the elastic part; and the fabric part configured to enclose the user's nose and the user's mouth by forming a sealing area between a lower lip area and a nasal bridge area, having a first surface that adheres to and is partially connected to an outer surface of the elastic part, and a second surface away from the elastic part for sealing at least a portion of the nasal bridge area; in which the fabric part consists of an inner edge adjacent to the fourth opening and an outer edge away from the fourth opening, the inner edge being smaller than or equal to the fourth opening of the elastic part, and the inner edge of the fabric part also including a hanging portion.

In one embodiment, the rigid part is made of a first material, the elastic part is made of a second material, and the fabric part is made of textile material, the first material being polycarbonate, and the second material being silicone with a hardness at or between 30 A to 70 A on the Shore scale.

In one embodiment, the first surface of the fabric part and the outer surface of the elastic part are directly connected and non-detachable by being directly connected by at least one of silicone adhesive, heat pressing, or molding.

In one embodiment, the outer edge of the fabric part is larger than an outermost annular projection of the elastic part in an X-axis direction.

In another embodiment, a patient interface cushion with fabric for delivering pressurized breathing gas to a user's nasal and oral airways is provided. The patient interface cushion includes a rigid part configured to provide support to an elastic part, one end of the rigid part having a first opening configured to receive breathing gas from a CPAP device, and the other end featuring a second opening that communicates with an inner cavity of the elastic part; the elastic part configured to connect with the rigid part and provide an attachment surface for a fabric part, having a third opening adjacent to the rigid part that communicates with the second opening, and a fourth opening away from the rigid part configured to allow a user's mouth and a user's nose to enter the inner cavity of the elastic part; the fabric part configured to form a sealing area between a lower lip area and a nasal bridge area, having a first surface that is adjacent to an outer surface of the elastic part, a second surface away from the elastic part for sealing at least a portion of the face of the user, an inner edge adjacent to the fourth opening, and an outer edge away from the fourth opening; and an adhesive layer positioned between the outer surface of the elastic part and the first surface of the fabric part that connects the elastic part and the fabric part; in which the elastic part further comprises protruding pieces on the lateral nasal area for fitting against the nasal sidewalls, and the inner edge of the fabric part is larger than the fourth opening of the elastic part, both the elastic part and the fabric part being configured to jointly seal the user's face; and in which the fabric part has a degree of elasticity and adapts to a curvature change of the elastic part when subjected to pressure, and distances of displacements at different points on the second surface of the fabric part vary when a same level of pressure is applied to different points on the fabric part in an X-axis direction.

In one embodiment, the adhesive layer comprises a glue or double-sided tape layer, with a thickness at or between 0.01 to 0.3 mm.

In one embodiment, a surface area of the second surface of the fabric part is at least 3.5% of an outer surface area of the elastic part.

In one embodiment, the fabric part is single-layered and has a uniform thickness.

In another embodiment, a patient interface cushion with fabric for delivering pressurized breathing gas to a user's nasal and oral airways is provided. The patient interface cushion includes a rigid part configured to provide support to an elastic part, one end of the rigid part having a first opening configured to receive breathing gas from a CPAP device, and the other end featuring a second opening that communicates with an inner cavity of the elastic part; the elastic part configured to connect with the rigid part and provide an attachment surface for the fabric part, having a third opening adjacent to the rigid part that communicates with the second opening, and a fourth opening away from the rigid part configured to allow the user's mouth and the user's nose to enter the inner cavity of the elastic part; the fabric part configured to form a sealing area between a lower lip area and a nasal bridge area, having a first surface that is adjacent to an outer surface of the elastic part, a second surface away from the elastic part for sealing at least a portion of the user's face, an inner edge adjacent to the fourth opening, and an outer edge away from the fourth opening; and an adhesive layer positioned between the outer surface of the elastic part and the first surface of the fabric part that connects the elastic part and the fabric part; in which a curvature of the fabric part's first surface conforms to a curvature of the elastic part, and the fabric part has a degree of elasticity and adapts to a curvature change of the elastic part when subjected to pressure, with the second surface of the fabric part contacting at least a portion of the nasal bridge area; and in which the elastic part comprises protruding pieces on the lateral nasal area for fitting against the nasal sidewalls, and the inner edge of the fabric part is larger than the fourth opening of the elastic part, and both the elastic part and the fabric part are configured to jointly seal the user's face.

In one embodiment, a connection between the elastic part and the fabric part via the adhesive layer is detachable, and the adhesive layer is made of peelable adhesive or double-sided tape.

In one embodiment, the fabric part is multi-layered, and a layer adjacent to the elastic part is made of a low-permeability material to prevent the adhesive layer from seeping through to the second surface.

In one embodiment, the fabric part is cut into an approximately annular outline using laser, die-cutting, or ultrasonic methods, and the shape of the inner edge is triangular or teardrop-shaped.

In yet another embodiment, a patient interface cushion with fabric, designed to deliver pressurized breathing gas to a user's nasal and oral airways is provided. The patient interface cushion includes a rigid part configured to provide support to an elastic part, one end of the rigid part having a first opening configured to receive breathing gas from a CPAP device, and the other end featuring a second opening that communicates with an inner cavity of the elastic part; an elastic part configured to connect with the rigid part and provide an attachment surface for the fabric part, having a third opening adjacent to the rigid part that communicates with the second opening, and a fourth opening away from the rigid part configured to allow the user's mouth and the user's nose to enter the inner cavity of the elastic part; a fabric part configured to enclose the user's mouth and nose by forming a sealing area between a lower lip area and a nasal bridge area, having a first surface that is adjacent to an outer surface of the elastic part, a second surface away from the elastic part that seals at least a portion of the user's face, an inner edge adjacent to the fourth opening, and an outer edge away from the fourth opening. The fabric part having one or more of the following characteristics:
 (a) a surface area of the second surface being at least 3.5% of an outer surface area of the elastic part;
 (b) a water absorption time less than 30 seconds, according to the AATCC 79 test method;
 (c) a surface roughness of the second surface having a Ra value at or between 0.2 to microns; and
 (d) a thickness of the fabric part being at least 0.6 mm.

In one embodiment, the fabric part has a breathability rate of 0.5-30 $ft^3/min/ft^2$ when tested according to the ASTM D737 test method.

In one embodiment, a material of the fabric part is a combination of one or more of the following: cotton fibers, linen, polyester fibers, elastane fibers, nylon fibers, acrylic fibers, rayon fibers, and spandex fibers.

In one embodiment, a diameter of the first opening is at or between 10 to 45 mm, the first opening is smaller than the second opening, and the inner edge of the fabric part is smaller than or equal to the fourth opening.

In still another embodiment, a patient interface cushion with fabric for delivering pressurized breathing gas to a user's nasal and oral airways is provided. The patient interface cushion includes a rigid part configured to provide support to an elastic part, one end of the rigid part having a first opening configured to receive breathing gas from a CPAP device, and the other end featuring a second opening that communicates with an inner cavity of the elastic part; the elastic part configured to connect with the rigid part and provide an attachment surface for the fabric part, having a third opening adjacent to the rigid part that communicates with the second opening, and a fourth opening away from the rigid part configured to allow the user's mouth and the user's nose to enter the inner cavity of the elastic part; the fabric part configured to form a sealing area between a lower lip area and a nasal bridge area, having a first surface that is adjacent to an outer surface of the elastic part, a second surface away from the elastic part for sealing at least a portion of the nasal bridge area, an inner edge adjacent to the fourth opening, and an outer edge away from the fourth opening; and an adhesive layer positioned between the outer surface of the elastic part and the first surface of the fabric part that connects the elastic part and the fabric part, in which a connection between the elastic part and the fabric part via the adhesive layer is detachable, and an adhesive force provided by the adhesive layer to the fabric part is greater than a weight of the fabric part.

In one embodiment, a thickness of the fabric part is at least 0.6 mm and at most 3.5 mm.

In one embodiment, a width of the fabric part is at least 10 mm.

In one embodiment, the fabric part has a non-continuous shape.

Implementing this patient interface cushion with fabric as discussed herein has at least the following beneficial effects:

1. In some embodiments, fabric is combined with a complete patient interface cushion, creating a new type of cushion that includes fabric. By adjusting the shape and contour of the fabric part, the fabric can either make contact with the user's face independently or work in conjunction with the elastic part to create a seal to the user's face. Additionally, the connection between the fabric and the elastic parts is detachable, making it more convenient for manufacturers in terms of production and inventory management. They only need to prepare one type of patient interface cushion with identical rigid and elastic parts and can then create two distinct cushions through post-processing-one with fabric and one without. This gives users more choices and allows them to customize the cushion according to their needs, either installing or removing the fabric. Furthermore, the patient interface cushion without fabric is already a complete product in itself. The modular design, achievable through post-processing, makes it easier for manufacturers to manage inventory and storage, reducing warehousing costs. It also reduces the need for producing multiple types of patient interface cushions, lowering energy consumption and reducing $CO_2$ emissions, thereby contributing to the efforts to prevent a further increase in atmospheric concentrations of greenhouse gases.

2. Compared to existing technology that uses silicone to seal the face in patient interface cushions, fabric is more breathable and has the added advantage of being moisture-wicking and sweat-absorbent. It can also absorb some oils, making the wearer feel more refreshed and preventing skin sensitivity issues. Fabric also reduces the likelihood that the cushion will shift due to sweat or oils, a common issue with silicone. Additionally, fabric is more skin-friendly than silicone, enhancing the user's comfort and reducing the discomfort felt while undergoing treatment. This helps alleviate the user's mental state and results in better compliance. Moreover, the inclusion of the fabric reduces contact between the cushion's elastic part and the user's face, thereby extending the cushion's lifespan.

3. Moreover, compared to existing silicone patient interface cushions, the embodiments discussed herein use a fabric component that offers particular advantages for certain user groups, such as those with beards or facial indentations due to injuries. The softer fabric can fill in gaps and contours, like the small protrusions formed by facial hair. In contrast, with one-piece elastic components, gaps can form around the beard area when the elastic component is in contact with the face, reducing the sealing performance of the patient interface cushion. The softer fabric is more adaptable to the facial contours and, under the pressure of the face, can fill in the gaps around the beard area to achieve better sealing.

4. Compared to existing technologies for mask liners or cushions, in some embodiments, the patient interface cushion combines the advantages of both the elastic part and the fabric part, while also securing the fabric part to the elastic part. This ensures that the curvature of the second surface of the fabric part conforms to the curvature of the outer surface of the elastic part, enabling better fit to the contours of the human face. The fixed attachment between the fabric and elastic parts prevents the fabric from wrinkling due to head movement or facial muscle changes during sleep, which could otherwise lead to air leakage and decreased treatment effectiveness. Since the fabric part is attached to the elastic part as part of the overall patient interface cushion, the steps for use are simplified. There's no need for the tedious adjustment of mask liners or cushions, making it more convenient for the user.

5. Compared to existing foam interface cushions, the manufacturing process of this disclosure is simpler, as this interface cushion has a lower defect rate, and is more cost-effective. The research and production processes for foam interface cushions are challenging and involve foreseeable difficulties with foam materials, foam shapes, and the bonding of foam material with silicone. First, the choice of foam material is critical. It requires finding the right softness and firmness through various ratio tests to ensure that the foam's permeability does not affect treatment effectiveness. Additionally, a new silicone material must be developed to support the foam part, followed by a series of tests to determine the foam's height, shape, and contour in relation to the silicone part. Secondly, in terms of production, the molding and manufacturing cycles for foam materials are longer compared to plastics and silicones. The general production process for foam involves creating a cube through a foaming process, dividing it into suitable thickness, shaping it through cutting or molding, and then joining it with the silicone part. Each step is challenging, and a mistake in one step can impact subsequent production steps. In contrast, this disclosure utilizes common, comfortable fabrics found in everyday life. The desired shape can be achieved simply by cutting the fabric, which is then attached to the elastic part to complete the molding process. Compared to foam interface cushions, this disclosure simplifies the production process, saving on research and production costs. Fewer manufacturing steps also mean a lower likelihood of errors and, consequently, a lower defect rate for the product.

DETAILED DESCRIPTION

Figure 1:
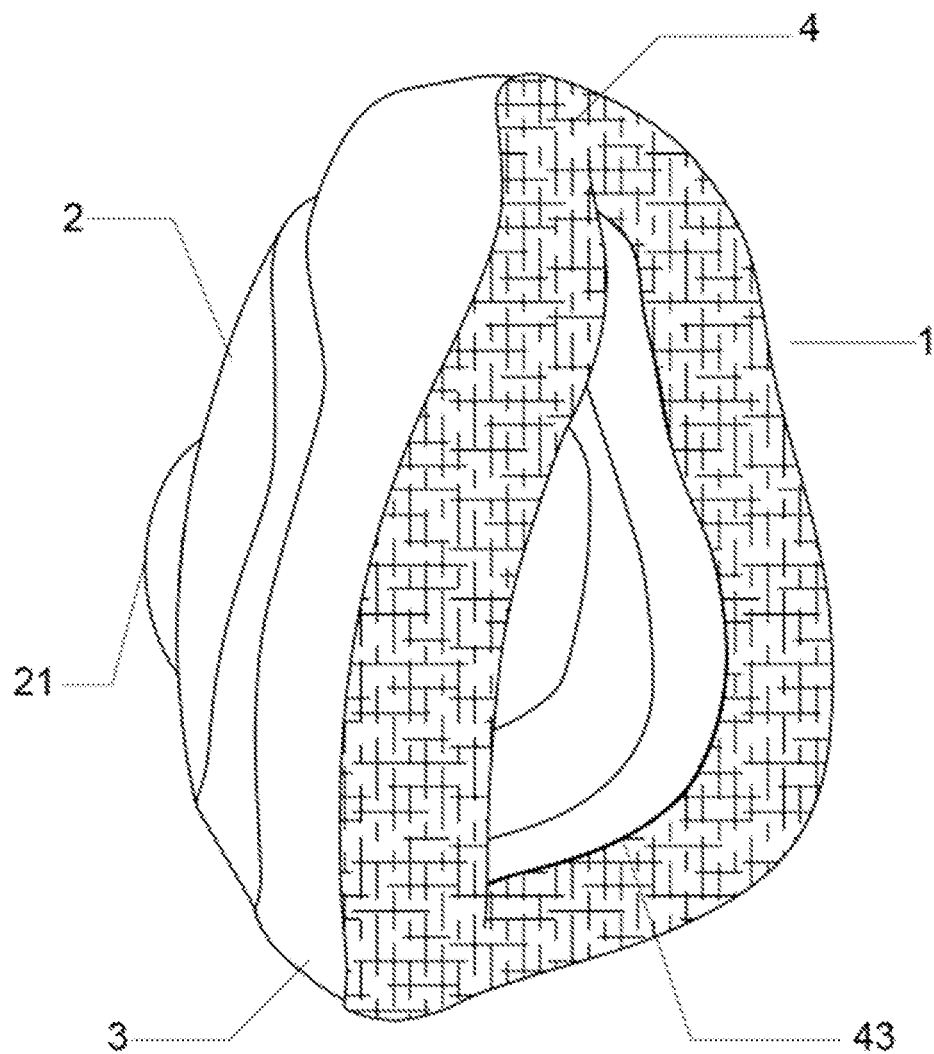
FIG. 1 is a structural schematic diagram of a patient interface cushion according to an embodiment.
Figure 2:
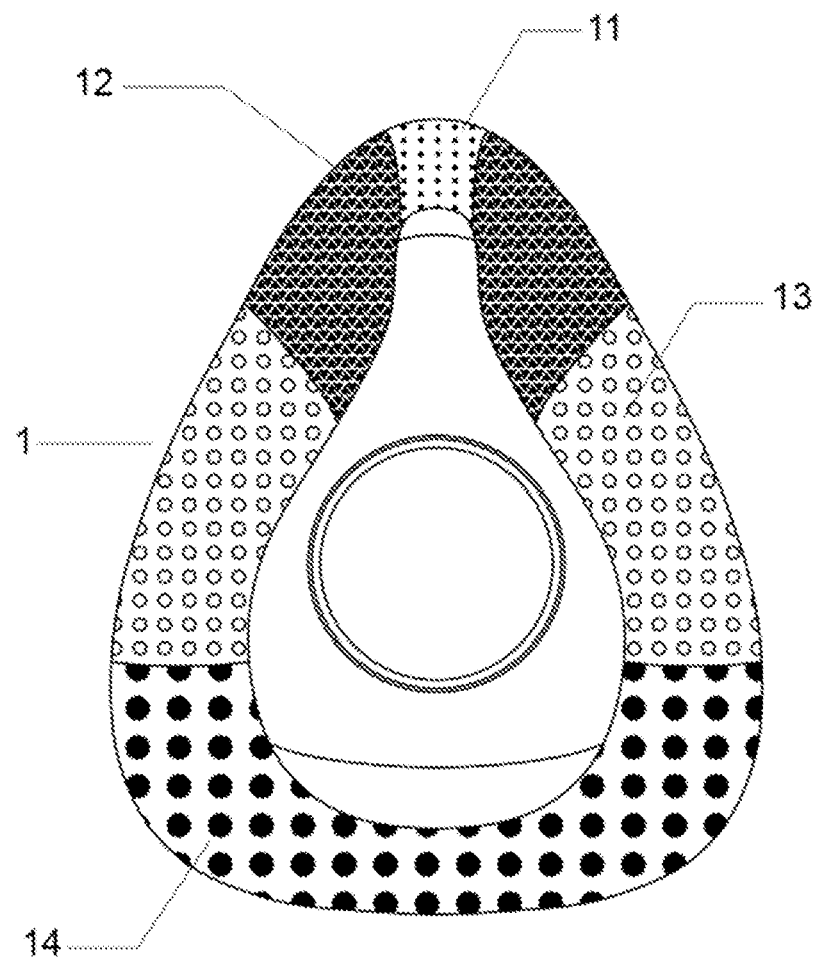
FIG. 2 is a schematic diagram of the region divisions for the patient interface cushion according to an embodiment.

To make the aforementioned objectives, features, and advantages of this disclosure clear and easy to understand, the following provides a detailed explanation of specific embodiments in conjunction with the accompanying drawings. Many specific details are elaborated upon in the description below to provide a thorough understanding of the present disclosure. However, the disclosure can be implemented in many different ways than those specifically disclosed here. Those skilled in the art can make similar improvements without departing from the spirit of the disclosure, and therefore, the disclosure is not limited to the specific embodiments disclosed below.

This disclosure aims to solve various issues associated with traditional patient interface cushions made of silicone, which are not breathable and can cause the user's face to become oily and sweaty. This can lead to the displacement of the interface cushion, affecting its sealing capability. Additionally, the disclosure addresses the shortcomings of existing foam interface cushions, which are prone to damage and have high manufacturing costs, as well as issues with mask liners and mask covers that can easily wrinkle and are uncomfortable to wear. The disclosure offers a patient interface cushion that incorporates fabric to make contact with the user's face. The fabric is designed to absorb sweat and oil and is more breathable, enhancing the comfort of the user. This alleviates the sense of distress being experienced during treatment and improves the user's emotional state during treatment, thereby resulting in better treatment adherence.

The following elaborates on the various structures of this disclosure's patient interface cushion with fabric, using various embodiments.

Embodiment 1

FIGS. 1 to 5 illustrate an example embodiment in which the patient interface cushion 1 includes a rigid part 2, an elastic part 3, a fabric part 4, and an adhesive layer 5. The patient interface cushion 1 has a first end and a second end, both of which have an opening. The opening at the first end is for receiving pressurized gas, and the opening at the second end provides an entry point for the user's mouth and nose into the cavity of the patient interface cushion. The upper end of the patient interface cushion contacts the user's nasal bridge area, and the lower end contacts the user's chin area, achieving a seal around the intervals between the nasal bridge and the chin. The contact areas of the patient interface cushion 1 with the face can be divided into the nasal bridge area 11, the lateral nose area 12, the cheek area 13, and the chin area 14. Given that the nasal bridge and chin areas have more contours compared to other parts of the face, the elasticity coefficient of the various parts of the patient interface cushion 1 differ. Therefore, when applying equal pressure in the same direction, e.g., at the same level, to different points on the patient interface cushion 1, the displacement distance at those points will vary.

The rigid part 2 is configured to support the elastic part 3. The rigid part 2 is made of a first material formed through injection molding. The first material is of plastic composition, and to better support the elastic part 3, a hard plastic material is preferred (which has higher hardness and is not easily deformed), such as high-density polyethylene, polypropylene, polycarbonate, polystyrene, etc. In this embodiment, the first material is polycarbonate. The rigid part 2 has a first opening 21 at one end to connect to a Continuous Positive Airway Pressure device for breathing gas. The other end has a second opening 22 that communicates with the inner cavity of the elastic part 3. Between the first opening 21 and the second opening 22, there are sidewalls that guide the airflow toward the elastic part 3. Near the second opening 22, there is a joint part that connects with the elastic part 3. The size and shape of the first opening 21 are determined by the frame or elbow joint that connects with the patient interface cushion. Typically, the diameter of the first opening 21 can be at or between 10 to 45 mm. The shape and size of the second opening 22 are determined by the contour where the elastic part 3 and rigid part 2 join, typically being ring-shaped, and the first opening 21 is smaller than the second opening 22. The sidewalls can be continuous and uniform, but they can also have intentional leakage holes that do not affect treatment effectiveness for the venting of exhaled waste gases. They may also have protrusions or indentations as positioning and securing configuration used for the positioning or securing of the frame or elbow joint (On the frame or elbow joint, indentations or protrusions are configured to accommadate the positioning and securing configuration, and the positioning and securing configuration is used for positioning or securing the frame or elbow joint when patient interface cushion is connected with the frame or elbow joint). Additionally, other functional interfaces, such as oxygen interfaces, can be included.

The elastic part 3 is configured to connect with the rigid part 2 and provide an attachment surface for the fabric part 4. The elastic part 3 is made of a second material and is directly joined to the rigid part 2 through molding or co-molding. At this point, it forms a complete patient interface cushion that delivers pressurized gas to both the user's nasal and oral airways. The second material is softer and more deformable than the first material, capable of conforming to the changing contours of the face. It is usually made from a flexible material with a Shore hardness at or between 30 A to 70 A, such as silicone, rubber, or elastic plastic. Preferably, it's made from biocompatible material with a Shore hardness between 35 A and 50 A. In this embodiment, the second material is silicone with a Shore hardness at or between 30 A to 70 A on the Shore scale. The elastic part 3 can be divided into a connection area that attaches to the rigid part 2, an attachment area that joins with the fabric part 4, and other transitional areas. The elastic part 3 has a third opening 31 adjacent to the rigid part 2 and in communication with the second opening 22. The third opening 31 is located in the connection area of the elastic part and is for receiving pressurized gas. The elastic part 3 also has a fourth opening 32 facing towards the face and away from the rigid part 2, allowing the user's mouth and nose to enter its inner cavity. The wall thickness of the elastic part 3 can be either single-layered or multi-layered, with varying thicknesses. Typically, at least one thin area is present in the elastic part 3, corresponding to either the nasal bridge area 11 or the chin area 14, which means that the wall thickness is thinner compared to non-thin areas (except for the thin area). This thin area has a greater capacity for elastic deformation because the nasal bridge area 11 or the chin area 14 experience greater contour changes than other facial areas. Therefore, these thin areas are designed to better conform to the skin's contours and contact the skin. Furthermore, the elastic part 3 has protruding pieces 33 in the lateral nasal area 12, which are formed by extending inward from the edge of the fourth opening 32 of the elastic part 3 and is configured to adhere to the nasal sidewalls (sidewalls on both sides of the nose). This ensures a better fit of the patient interface cushion to the face, enhancing the mask's airtightness and preventing gas leakage.

Figure 15:
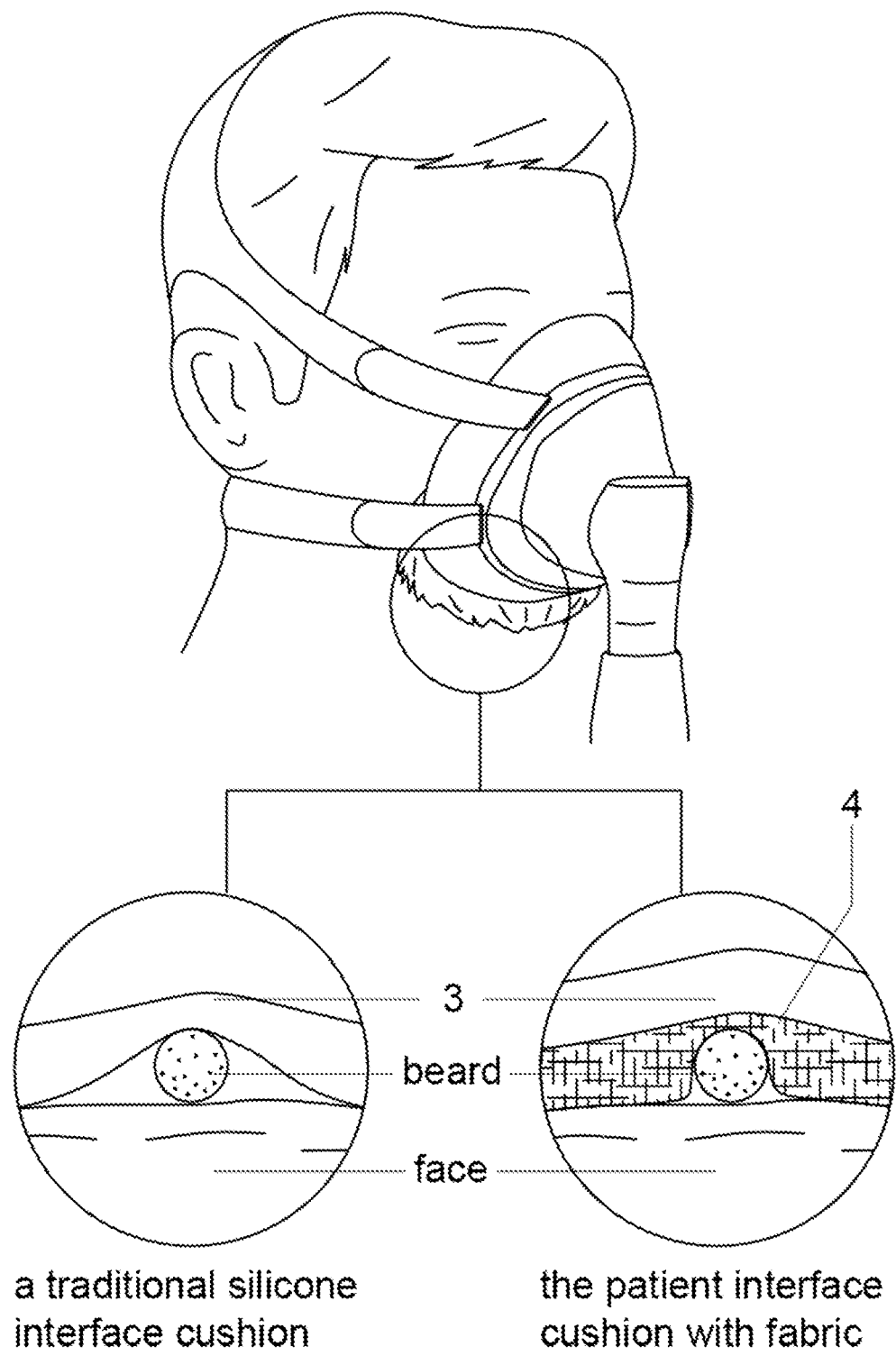
FIG. 15 is an enlarged schematic diagram showing the wearing state of the patient interface cushion in an embodiment.

The fabric part 4 is designed to enclose the user's nose and mouth and form a sealed area between the lower lip and nasal bridge areas. It is made of textile material, offering the advantages of high absorbency and breathability. This effectively absorbs the user's facial secretions overnight, making the user feel dry and comfortable, thereby increasing the tolerance for mask usage. The textile material can be composed of natural fibers like cotton, linen, silk, or wool; synthetic fibers like polyester fibers (polyester), elastane fibers (spandex), nylon fibers, acrylic fibers, rayon fibers, and spandex fibers; or even non-woven fabric. It can also be a blend of two or more of these fibers, for example, a mix of cotton and elastane fibers, spandex and elastane fibers, acrylic and nylon fibers, or a combination of spandex, acrylic, and rayon fibers. It can also be integrated with metallic fibers to create functional fabrics, such as antibacterial or anti-static fabrics. In this embodiment, the material for the fabric part 4 can be a blend of one or more of the following: cotton fibers, linen, polyester fibers, elastane fibers, nylon fibers, acrylic fibers, rayon fibers, and spandex fibers. Since the permeability of the patient interface cushion 1 should be lower than 20 L/min, there are certain requirements for the breathability of the fabric part 4. It needs to offer comfort to the user without allowing excessive gas leakage. The fabric part 4 has an air permeability of 0.5-30 ft$^3$/min/ft$^2$ when tested according to the ASTM D737-18 test method. In another embodiment, the air permeability is about 15-60 ft$^3$/min/ft$^2$ or 50-80 ft$^3$/min/ft$^2$. Additionally, the fabric part 4 needs to absorb sweat from the user's face, so it should also meet certain requirements for water absorption. According to the AATCC 79-2018 test method, the absorption time is less than 30 seconds, preferably less than 20 seconds, and most preferably less than 10 seconds. The role of fabric part 4 is to provide the user with a more comfortable experience (compared to the elastic part 3, the fabric is more skin-friendly and comfortable for the user), and to enhance sealing (the fabric has better deformability and can fill in facial grooves, as shown in FIG. 15.) The fabric part 4 can be made of lightweight, soft, and smooth materials to avoid adding extra weight to the patient interface cushion 1 or causing discomfort. The yarn count of fabric part 4 can be no less than 30 and no higher than 100.

Figure 4:
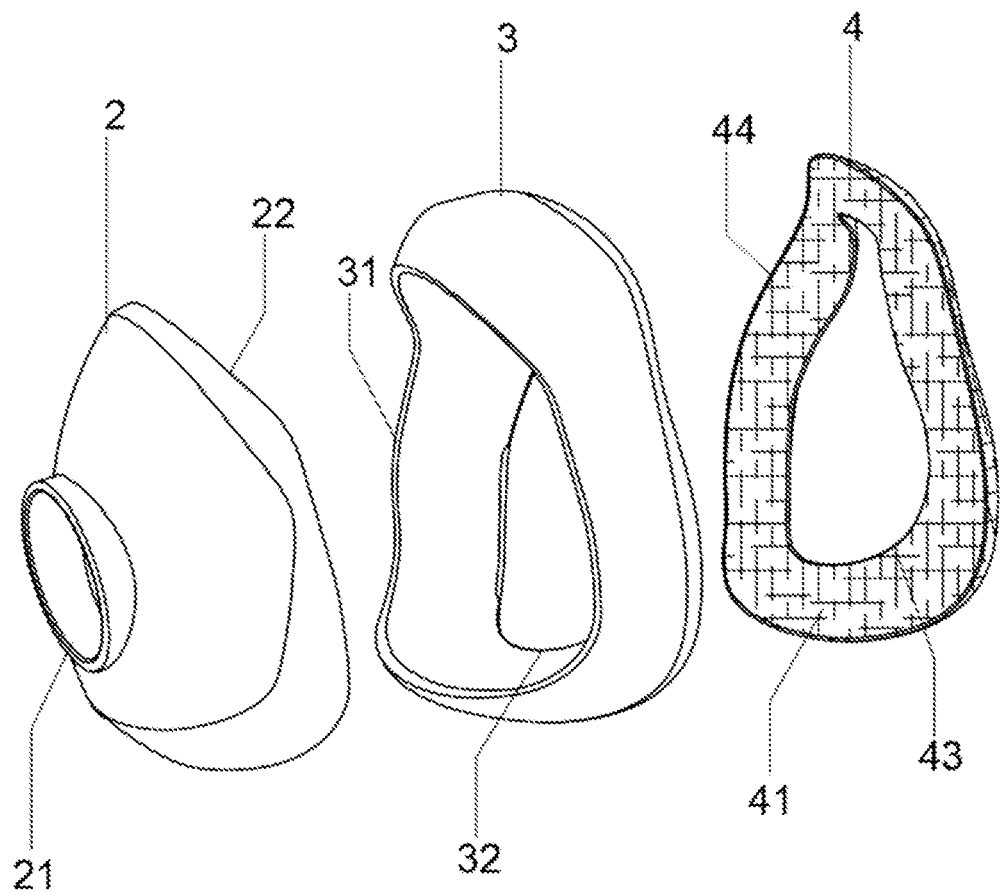
FIG. 4 is an exploded structural schematic diagram of the patient interface cushion according to an embodiment.
Figure 5:
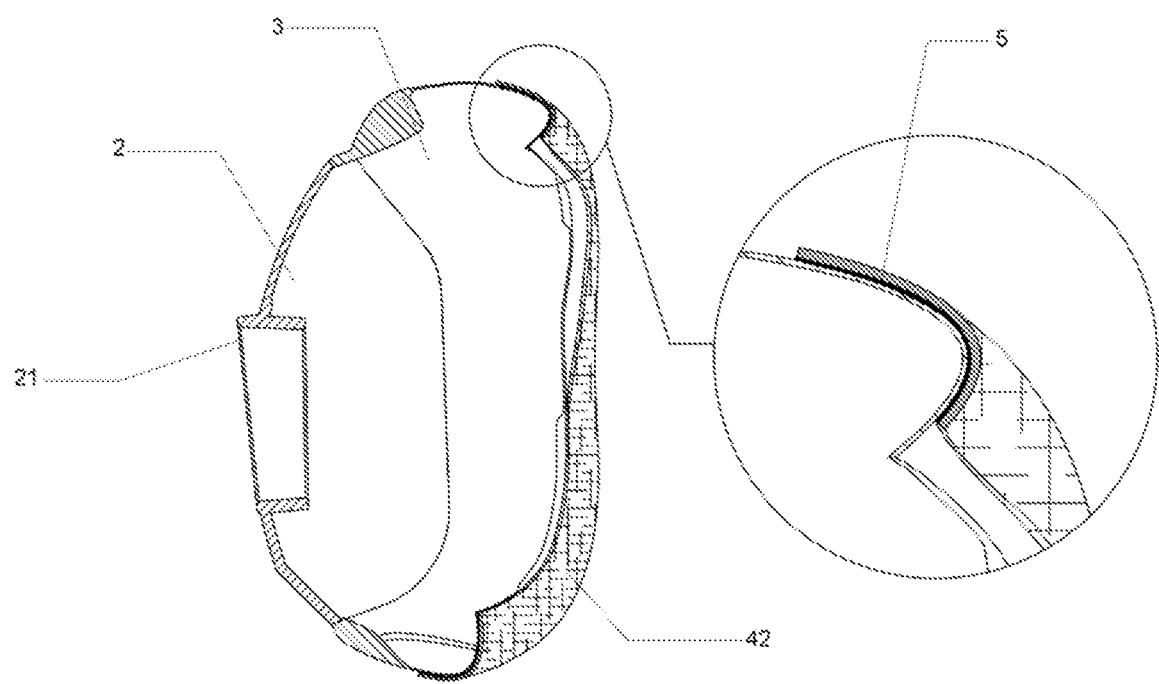
FIG. 5 is a cross-sectional schematic diagram of the patient interface cushion in the Y-axis direction, according to an embodiment.
Figure 7:
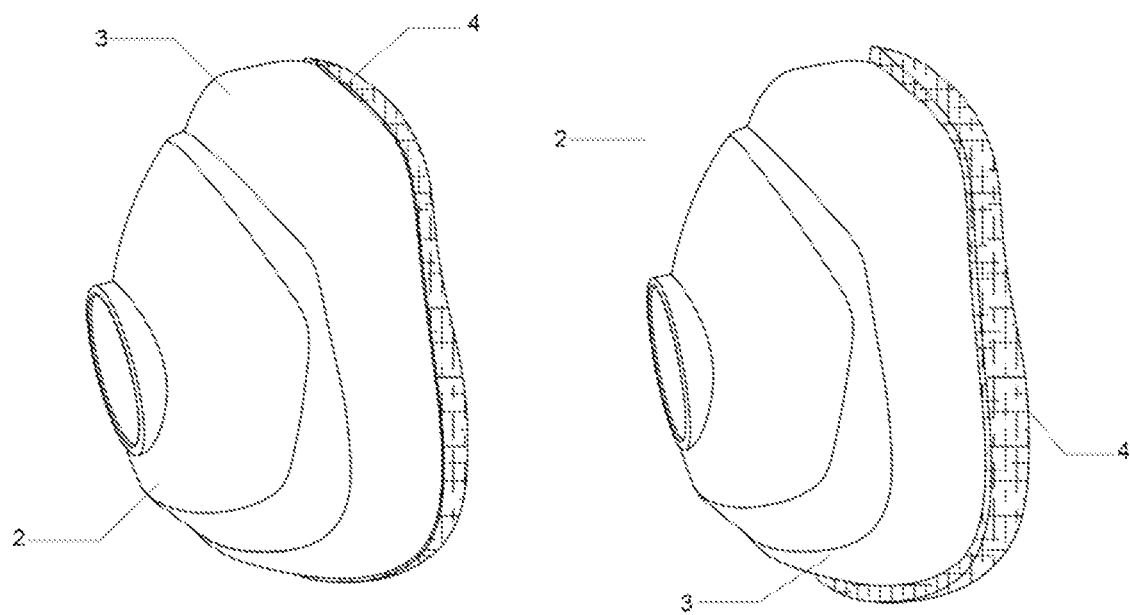
FIG. 7 is a schematic diagram indicating different thicknesses of the fabric part according to an embodiment.
Figure 8:
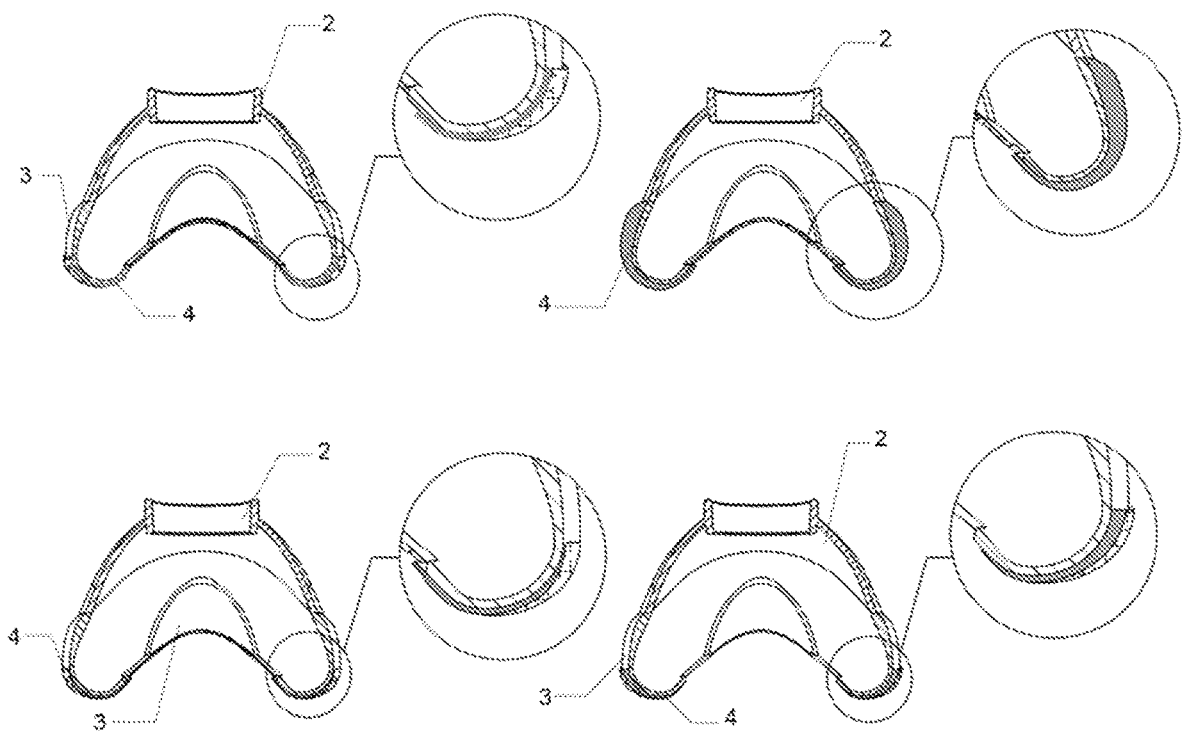
FIG. 8 is a structural diagram of the cross-section in the Z-axis direction of the patient interface cushion according to various embodiments.
Figure 9:
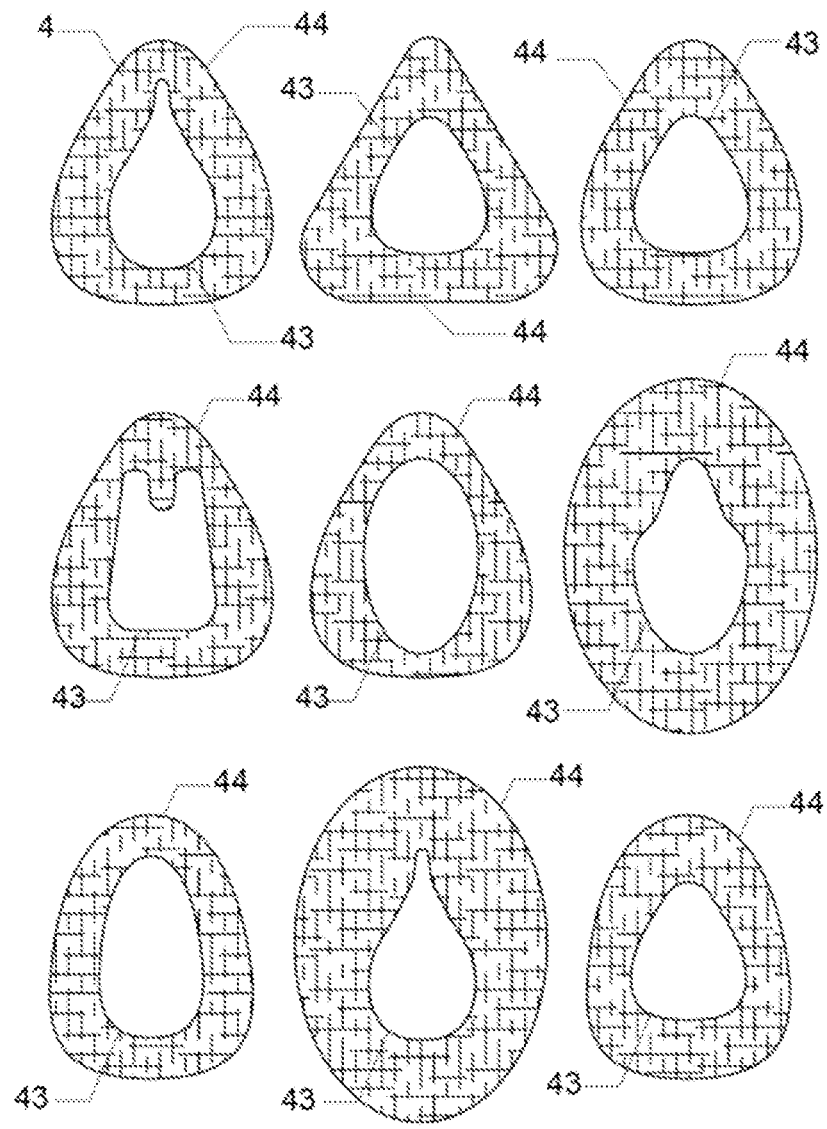
FIG. 9 is the plan views of the fabric part according to various embodiments.
Figure 11:
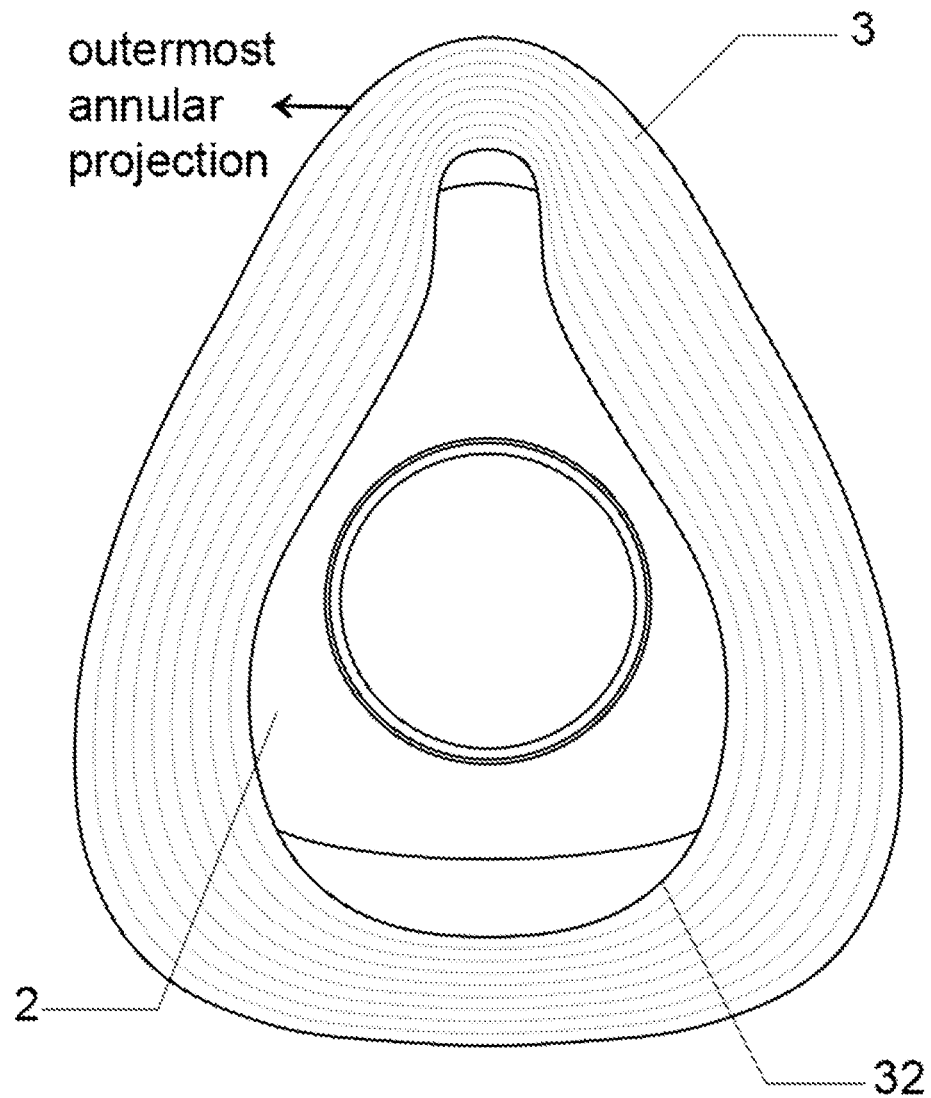
FIG. 11 is a projection schematic diagram of the rigid part and the elastic part in the X-axis direction as shown in FIG. 3.

The fabric part 4 has a first surface 41 that is adjacent to and partially connected to the outer surface of the elastic part 3, and a second surface 42 that is far away from the elastic part 3 and seals at least a portion of the user's face. More specifically, the second surface 42 of the fabric part 4 at least contacts a part of the user's nasal bridge. The Ra value (average surface roughness) of the second surface 42 is at or between 0.2 to 10 micrometers. The fabric part 4 is partially elastic and will conform to changes in the curvature of the elastic part 3 when pressure is applied. When equal pressure is applied to different points on the fabric part 4 along the X-axis, the distance of displacement at different points on the second surface 42 will vary. As shown in FIGS. 1, 4, and 9, the fabric part 4 has an inner edge 43 adjacent to the fourth opening 32 and an outer edge 44 that is far away from the fourth opening 32. The shape of the inner and outer edges can be approximately triangular, elliptical, teardrop-shaped, or any other shape that can cover the elastic part 3. The shapes of the inner edge 43 and outer edge 44 do not necessarily have to be the same; for example, the inner edge could be teardrop-shaped while the outer edge is triangular, or the inner edge could be teardrop-shaped while the outer edge is elliptical. The shape can be freely combined, as long as the inner edge 43 can provide an opening for the user's mouth and nose to pass through. In this embodiment, the fabric part 4 is cut into roughly an annular contour, which is continuously connected from beginning to end, through laser, die-cutting, or ultrasonics, wherein the shape of the inner edge 43 is approximately triangular or teardrop-shaped. The inner edge 43 is equal to or smaller than the fourth opening 32 of the elastic part 3. The fabric part 4 at the inner edge 43 has a hanging portion, and the outer edge 44 of the fabric part 4 is larger than the outermost annular projection of the elastic part 3 in the X-axis direction (as shown in FIG. 11), implying that, at this time, it is in complete contact with the user's face by the fabric part 4. The hanging portion of the inner edge 43 can be blown up under the action of pressurized gas to fit the face more closely, enhancing the air-tightness of the patient interface cushion 1, and the fabric part 4 alone seals the user's face, providing better comfort. As shown in FIG. 8, the thickness of the fabric part 4 can be uniform or variable; for example, it can gradually thin out at the outer edge 44 to fit the elastic part 3 or thin out at the inner edge 43 to reduce their presence on the face. In this embodiment, the fabric part 4 is single-layered and has a uniform thickness. The fabric part 4 cannot be too thin; otherwise, the user will feel the elastic part 3, losing the soft comfort added by the fabric part 4, so the thickness of the fabric part 4 is at least 0.6 mm. If the fabric is too thick, leakage may occur as the increased thickness enlarges the area of gas penetration; therefore, to ensure the sealing effect of the patient interface cushion 1, the thickness of the fabric part is at most 3.5 mm, as illustrated in FIG. 7, which shows the fabric part 4 with different thicknesses.

The adhesive layer 5 can be a connecting layer set between the outer surface of the elastic part 3 and the first surface 41 of the fabric part 4. It is used for connecting the elastic part 3 and the fabric part 4. The adhesive layer 5 can be glue or double-sided tape. Several factors need to be considered when choosing the material for the adhesive layer 5: (a) bonding strength, (b) material properties, (c) appearance, and (d) environmental friendliness.

(a) The bonding strength needs to ensure that the connection between the elastic part 3 and the fabric part 4 is sufficiently secure. It should guarantee that, in the absence of external forces, the adhesive force provided by the adhesive layer 5 to the fabric part 4 is greater than the weight of the fabric part 4. Moreover, the bonding should be strong enough to prevent detachment or air leakage due to movement during sleep or wrinkling. At the same time, the bonding strength should not be excessively strong to avoid making disassembly user-unfriendly or risk damaging the materials.

(b) Material characteristics for the adhesive layer 5 include whether the material is biocompatible, whether it can bond with the materials of the elastic part 3 and the fabric part 4, and whether it will permeate the fabric part 4. Since the patient interface cushion 1 comes into contact with the human body, it is crucial to ensure that the material for the adhesive layer is safe for human contact and complies with local regulations, such as ISO 10993 standards. Due to the significant differences in the materials used for the elastic part 3 and the fabric part 4—for example, common glues or double-sided tapes in the market are used for bonding paper, wood, plastic, and metal—it's essential to choose a material of the adhesive layer 5 that can effectively bond both materials of the elastic part 3 and the fabric part 4 without altering their chemical or physical properties. Additionally, once the adhesive layer 5 solidifies from its fluid state, its hardness should not exceed that of the elastic part 3 to avoid applying uncomfortable pressure on the user's face. Moreover, when the adhesive layer 5 is in its initial fluid state, it's important to consider whether it will permeate the fabric part 4. If it seeps through to the fabric's second surface 42, it could negatively affect the fabric's characteristics, making it feel stiff and uncomfortable for the user.

(c) The appearance concerns two aspects. On one hand, the color of the adhesive layer 5 should not be overly unusual or give the impression of a product flaw to the user. Some adhesives currently in use can "whiten" under conditions of insufficient ventilation or other operational issues (i.e., they turn white when they dry, leaving a white residue). Such residues should be avoided as they would affect the final appearance of the patient interface cushion 1. Additionally, the adhesive should not have a strong, irritating odor that might disturb the user.

(d) Environmental considerations involve two aspects. On one hand, there's the lifespan of the adhesive layer 5, such as how many times it can be washed or disassembled before losing its bonding strength. On the other hand, there's the environmental impact; ideally, the adhesive layer 3 should be eco-friendly and harmless to the environment. Therefore, the choice of adhesive is crucial. Brands like 3M, Loctite, and UHU could be considered for their glues or double-sided tapes.

In summary, the choice of adhesive layer 5 can be crucial. In this embodiment, the adhesive layer 5 is either glue or double-sided tape with a thickness of 0.01-0.3 mm. More specifically, the adhesive layer 5 is a peelable glue or double-sided tape.

Figure 3:
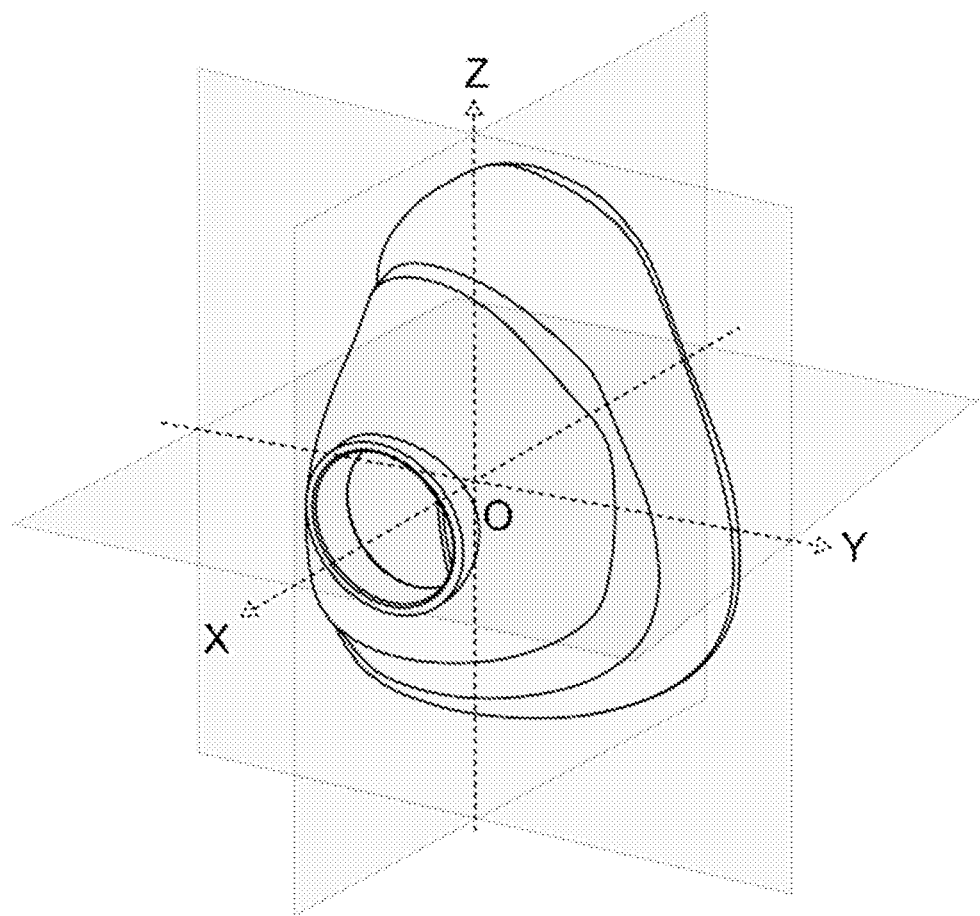
FIG. 3 is a schematic diagram indicating the orientation of the patient interface cushion according to an embodiment.
Figure 6:
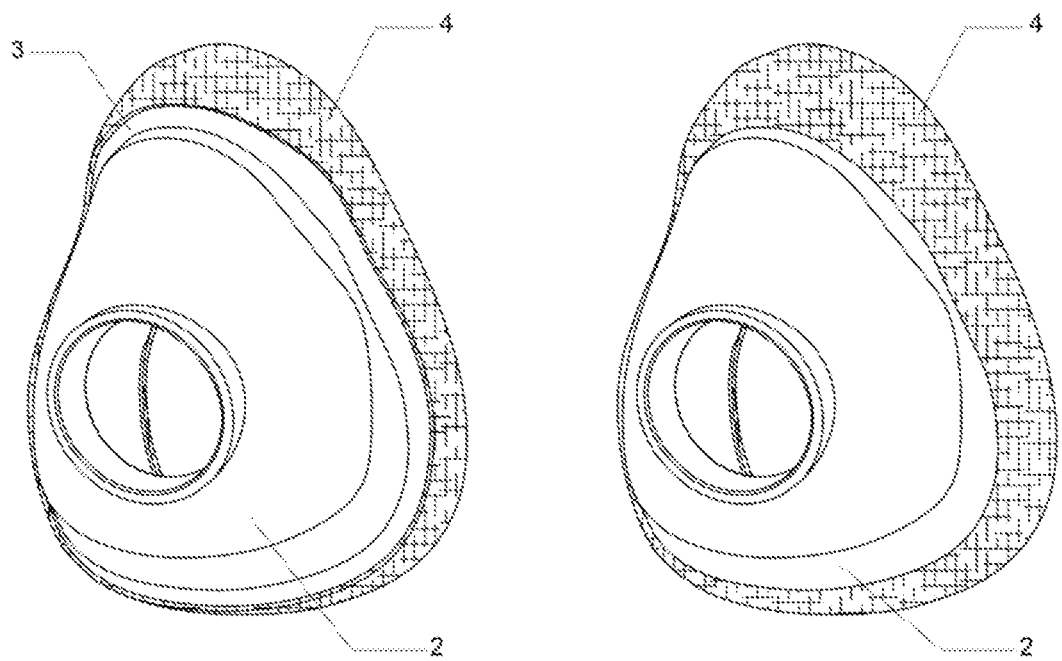
FIG. 6 is a schematic diagram showing different coverage areas of the fabric part according to an embodiment.
Figure 10:
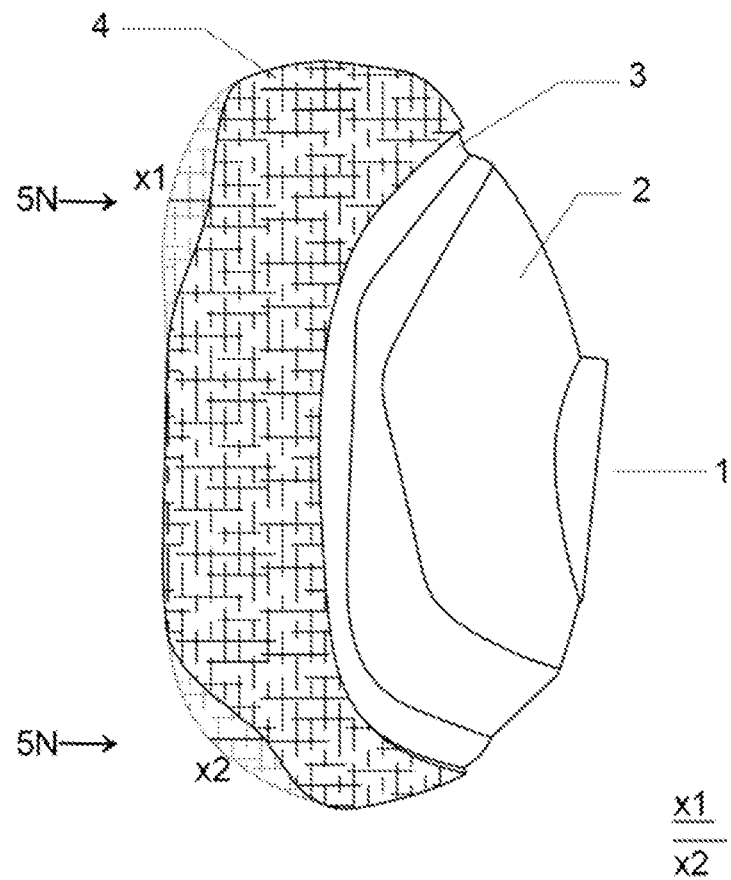
FIG. 10 is a schematic diagram illustrating the forces acting on the patient interface cushion according to an embodiment.

The connection between the elastic part 3 and the fabric part 4 through the adhesive layer 5 may be detachable. This allows users to choose whether or not to use the fabric part 4 freely. When the fabric part is removed, a conventional patient interface cushion without the fabric is obtained. This not only offers an additional option but also extends the lifespan of the patient interface cushion. In other embodiments, the connection between the elastic part 3 and the fabric part 4 through the adhesive layer 5 is non-detachable, for example, through the use of hot melt adhesive, silicone adhesive, or permanent glue. When the fabric part 4 adheres to the elastic part 3, the curvature of the first surface 41 of the fabric part 4 conforms to the curvature of the elastic part 3. The fabric part 4 has some elasticity, and when connected to the elastic part 3, it should be in a relaxed state (i.e., not stretched or deformed by external forces) and cover the outer surface of the elastic part 3. Since the fabric part 4 has greater deformability than the elastic part 3, it can adapt to the deformation of the elastic part 3 and conform to its shape. In other words, when subjected to pressure, the fabric part 4 adjusts according to the changes in the curvature of the elastic part 3. In another embodiment, the fabric part 4 can be partially stretched to cover the outer surface of the elastic part 3. It should be noted that the fabric part 4 should cover the contact area of the patient interface cushion 1. Specifically, the inner edge 43 should be smaller than or equal to the fourth opening 32 to ensure that the opening at the inner edge 43 of the fabric part 4 can be passed through by the user's mouth and nose. The distance projected onto the YOZ plane (as shown in FIG. 3, in the three-dimensional Cartesian coordinate system, the plane where the Y-axis and Z-axis are located) from points on the inner edge 43 and points on the fourth opening 32, which are on the same side and on the same straight line, is at most 20 mm. However, the outer edge 44 can be of any size. As shown in FIGS. 1 and 6, the outer edge 44 may cover only the outermost annular projection of the elastic part 3 in the X-axis direction, or it can completely cover the elastic part 3, or even extend beyond the elastic part 3 to cover the rigid part 2. Because the wall thickness of the elastic part 3 is not uniform, and both the elastic part 3 and fabric part 4 have a certain degree of elasticity and deformability, the displacement distances (x) at different points on the second surface 42 of the fabric part 4 vary when the same amount of pressure (or level) (e.g., 5N) is applied to different points on the fabric part 4 in the X-axis direction, as shown in FIG. 10.

Embodiment 2

This embodiment of a patient interface cushion with fabric is designed to supply pressurized breathing gas to the user's nasal and oral airways. It includes a rigid part 2, an elastic part 3, and a fabric part 4. The difference between the patient interface cushion 1 in this embodiment and the patient interface cushion in Embodiment 1 is that the patient interface cushion 1 does not include an adhesive layer 5. In this embodiment, the first surface 41 of the fabric part 4 and the outer surface of the elastic part 3 are directly connected and non-detachable. Methods of direct connection include silicone adhesive, heat pressing, or molding. The non-detachable direct connection between the elastic part 3 and the fabric part 4 has the following advantages: Firstly, the non-detachable connection means that there is no risk of the patient interface cushion 1 slipping off or detaching during sleep, even if movement occurs. Secondly, the non-detachable direct connection reduces the installation process for the user, thereby lowering the probability of air leakage due to improper installation or inaccurate positioning causing wrinkles in the fabric part 4. Lastly, removing the adhesive layer 5 can reduce costs.

Embodiment 3

Figure 13:
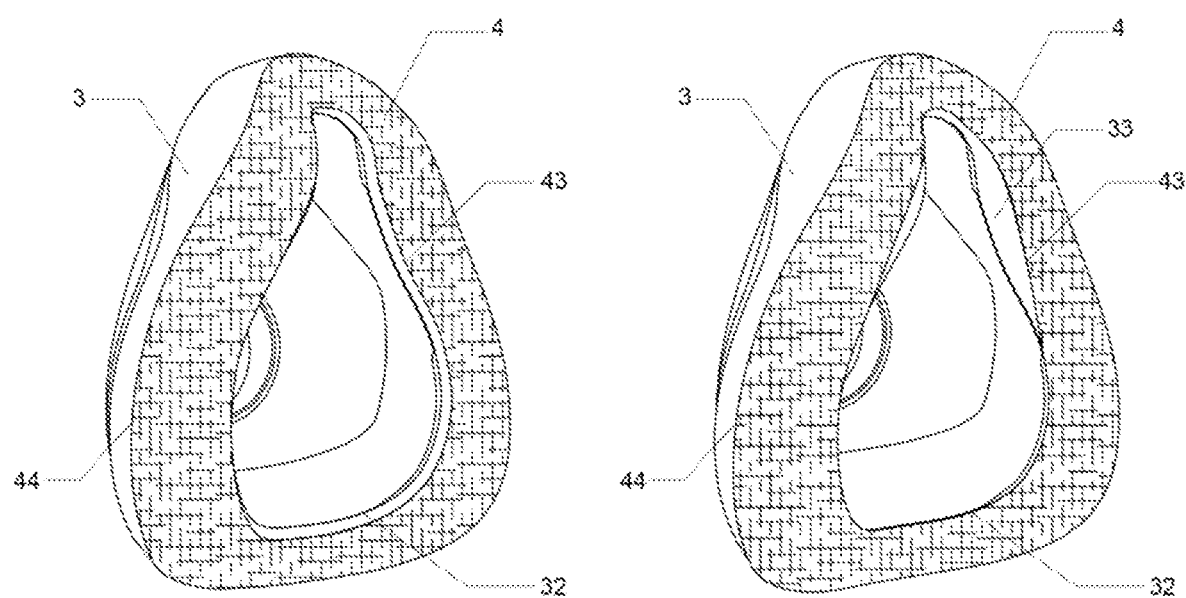
FIG. 13 is a structural schematic diagram of the patient interface cushion in yet another embodiment.

In this embodiment, the patient interface cushion with fabric is designed to supply pressurized breathing gas to the user's nasal and oral airways. It includes a rigid part 2, an elastic part 3, a fabric part 4, and an adhesive layer 5. The difference between the patient interface cushion 1 in this embodiment and the one in Embodiment 1 lies in the coverage range of the fabric part 4 over the elastic part 3. As shown in FIG. 13, the fabric part 4 in this embodiment is cut into a roughly annular contour (or outline) using laser, die-cutting, or ultrasonic methods, and the shape of the inner edge is roughly triangular or teardrop-shaped. The elastic part 3 features protruding pieces 33 on the lateral nasal area 12 to fit against the nasal sidewalls, and the inner edge 43 of the fabric part is larger than the fourth opening 32 of the elastic part 3, both the elastic part 3 and fabric part 4 configured to jointly seal the user's face. Due to the much lower breathability of the elastic part 3 compared to the fabric part 4, the combined sealing of the user's face by both the elastic part 3 and fabric part 4 can enhance the airtight effect of the patient interface cushion 1. At the same time, the fabric part 4 increases comfort by being in contact with the face. To provide a better user experience, the width of the fabric part 4 is at least 10 mm, and the surface area of the second surface 42 of the fabric part 4 is at least 3.5% of the outer surface area of the elastic part 3.

There can be several variations in the form by which the elastic part 3 and the fabric part 4 jointly seal the user's face: The first variation involves the inner edge 43 being larger than the fourth opening 32 throughout its entire circumference. The outer edge 44 is larger than or equal to the outermost annular projection of the elastic part 3 along the X-axis. In this case, the edge of the fourth opening 32 of the elastic part 3 and the fabric part 4 make joint contact with the face. The second variation involves the inner edge 43 being larger than the fourth opening 32 in the nasal bridge area 11 and the lateral nasal area 12, while being smaller or equal to the fourth opening 32 in the cheek area 13 or chin area 14. The outer edge 44 is also larger than or equal to the outermost annular projection of the elastic part 3 along the X-axis. In this design, the protruding pieces 33 of the elastic part 3 and the fabric part 4 make joint contact with the face. This design choice is made because the nose and face have varying heights, and the elastic part 3 provides better airtightness. Therefore, it is more effective for sealing the nasal bridge area 11 and the lateral nasal area 12 than the fabric part 4. The third variation involves the inner edge 43 being smaller or equal to the fourth opening 32, while the outer edge 44 is smaller than the outermost annular projection of the elastic part 3 along the X-axis. In this case, both the fabric part 4 and the part of the elastic part 3 that extends beyond the fabric part 4 make contact with the face. These are just a few examples of possible scenarios. These variations could be layered on top of each other or combined in any other way as needed.

In another implementation of this embodiment, the patient interface cushion with fabric does not include an adhesive layer 5. It is configured to supply pressurized breathing gas to the user's nasal and oral airways and consists of a rigid part 2, an elastic part 3, and a fabric part 4. In this design, the first surface 41 of the fabric part 4 directly contacts the outer surface of the elastic part 3. The fabric part 4 has a roughly annular contour, and its inner edge 43 is larger than the fourth opening 32. Both the protruding pieces 33 of the elastic part 3 and the fabric part 4 work together to seal the user's face.

Embodiment 4

Figure 12:
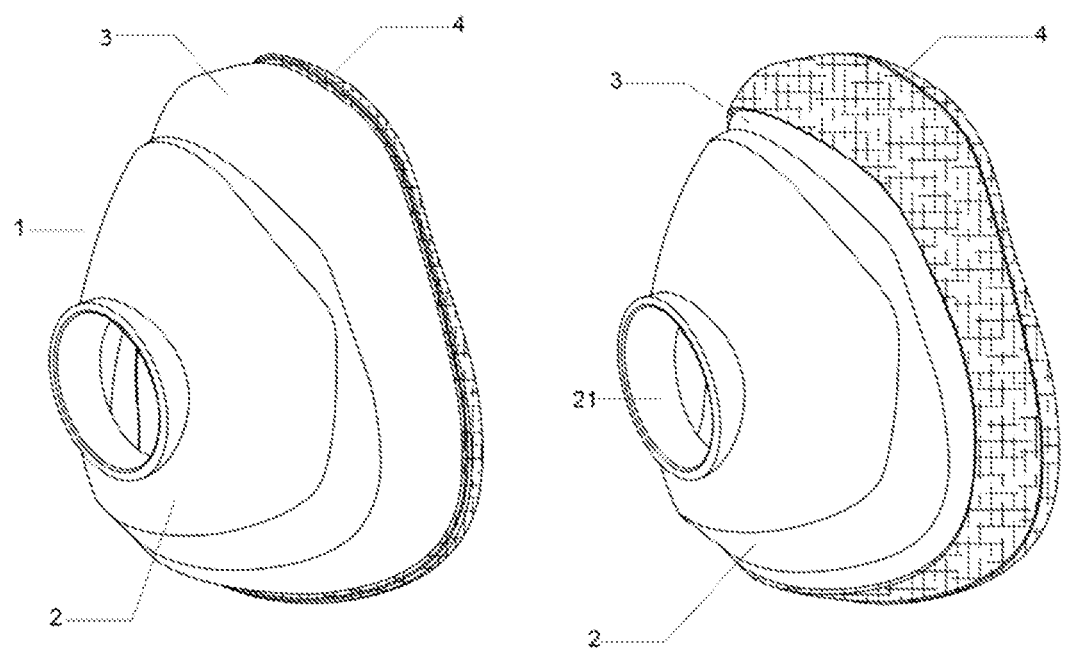
FIG. 12 is a structural schematic diagram of the patient interface cushion according to an embodiment.

In this embodiment, the patient interface cushion with fabric is designed to supply pressurized breathing gas to the user's nasal and oral airways. It consists of a rigid part 2, an elastic part 3, a fabric part 4, and an adhesive layer 5. The difference between this patient interface cushion and the one in Embodiment 1 lies in the number of layers in the fabric part 4. As shown in FIG. 12, the fabric part in this embodiment is multi-layered, consisting of either the same or different textile materials stacked together. These layers can be bonded by methods such as compression, stitching, thermoplastic compositing, hot-melt bonding, or film laminating. However, to maintain a proper seal and avoid leakage, the thickness of the fabric part should not exceed 3.5 mm, as an overly thick stack of fabric layers is prone to displacement and air leakage. At the same time, it shouldn't be too thin, as that would compromise the soft and comfortable characteristics of the fabric part 4; hence, the thickness of the fabric part must be at least 0.6 mm. Each layer of the multi-layered textile material can have the same or different sizes, thicknesses, and materials to achieve various functionalities. For example, the bottom layer (which is closest to the elastic part 3) could use a textile material that adheres well to the adhesive layer. Additional functional layers, such as anti-static fabric, could be added on top the bottom layer to improve the user experience by preventing static electricity. In some embodiments, considering that the adhesive layer 5 may have some permeability, a low-permeability material like nylon-coated fabric, polyurethane-coated fabric, or high-density polyethylene fabric is used for the layer closest to the elastic part 3 to prevent the adhesive layer from seeping through to the second surface 42. In this embodiment, the inner edge 43 is smaller than or equal to the fourth opening 32. In another embodiment, the inner edge 43 is larger than the fourth opening 32.

In another implementation of this embodiment, the patient interface cushion with fabric, which is designed to supply pressurized breathing gas to the user's nasal and oral airways, does not include an adhesive layer 5. Instead, it consists of a rigid part 2, an elastic part 3, and a fabric part 4. The fabric part 4 is multi-layered, and the first surface 41 of the fabric part 4 directly contacts the outer surface of the elastic part 3.

Embodiment 5

Figure 14:
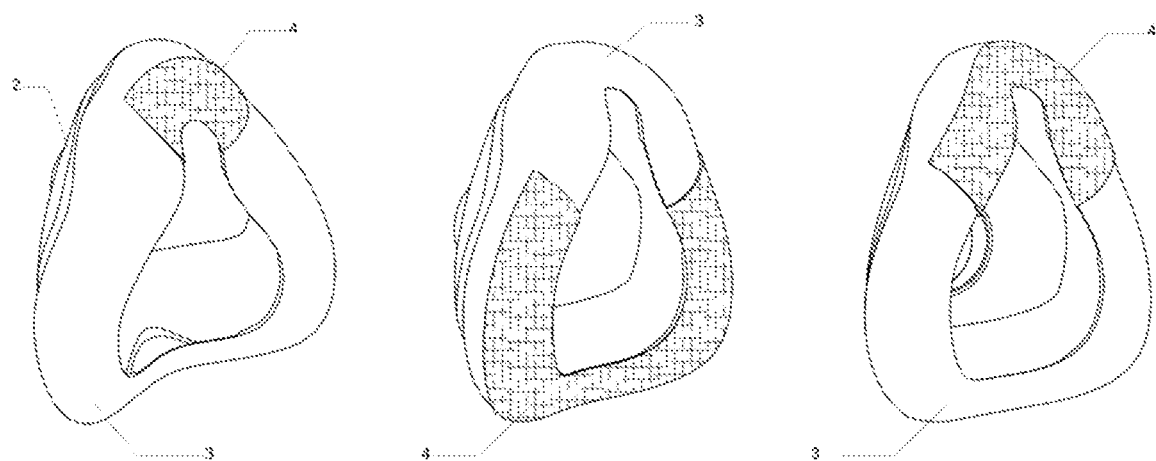
FIG. 14 is a structural schematic diagram of the patient interface cushion in yet another embodiment.

In this embodiment, the patient interface cushion with fabric is designed to supply pressurized breathing gas to the user's nasal and oral airways. It consists of a rigid part 2, an elastic part 3, a fabric part 4, and an adhesive layer 5. One difference between this patient interface cushion and the one in Embodiment 1 is that the fabric part has a non-continuous shape. As illustrated in FIG. 14, the fabric part 4 in this embodiment is not annular; it is configured to form a sealing area between the user's lower lip and nasal bridge areas. There are several variations of the fabric part 4: The first variation of the fabric part 4 covers only the nasal bridge area 11, where the fabric part 4 has a second surface 42 that is far away from the elastic part 3 to at least partially seal the user's nasal bridge. This design reduces pressure on the nasal bridge and minimizes red marks. Another variation of the fabric part 4 covers only the chin area 14, where the second surface 42 at least contacts the user's chin. The third variation of the fabric part 4 consists of two separate fabric parts, each contacting the cheek area 13, which means the second surface 42 at least partially contacts the user's cheeks, thereby alleviating the pressure sensation on the cheekbones.

Other variations of the fabric part 4 are also possible, such as not covering the nasal bridge area 11, which has significant height differences, and only covering flatter areas. For comfort reasons, the area of the fabric part 4 covering the elastic part 3 should not be too small, otherwise, the purpose of adding the fabric part 4 will be lost as the elastic part 3 will be in contact with the cheeks. Therefore, the surface area of the second surface 42 should be at least 3.5% of the outer surface area of the elastic part 3. In this scenario, the fabric part 4 is placed on the nasal bridge area 11, with the second surface 42 contacting the user's nasal bridge, and the outer edge 44 close to the outermost annular projection of the elastic part in the X-axis direction, as shown in FIG. 14. Another implementation of this embodiment is that the patient interface cushion does not include the adhesive layer 5. It includes a rigid part 2, an elastic part 3, and a fabric part 4, where the fabric part 4 has a non-continuous shape and the first surface 41 of the fabric part 4 directly contacts the outer surface 41 of the elastic part 3.

Implementing this patient interface cushion with fabric has at least the following beneficial effects:

1. The disclosure combines fabric with a complete patient interface cushion, creating a new type of cushion that includes fabric. By adjusting the shape and contour of the fabric part, the fabric can either make contact with the user's face independently or work in conjunction with the elastic part to create a seal to the user's face. Additionally, the connection between the fabric and the elastic parts can be detachable, making it more convenient for manufacturers in terms of production and inventory management. They only need to prepare one type of patient interface cushion with identical rigid and elastic parts and can then create two distinct cushions through post-processing-one with fabric and one without. This gives users more choices and allows them to customize the cushion according to their needs, either installing or removing the fabric. Furthermore, the patient interface cushion without fabric is already a complete product in itself. The modular design, achievable through post-processing, makes it easier for manufacturers to manage inventory and storage, reducing warehousing costs. It also reduces the need for producing multiple types of patient interface cushions, lowering energy consumption and reducing $CO_2$ emissions, thereby contributing to the efforts to prevent a further increase in atmospheric concentrations of greenhouse gases.
2. Compared to existing technology that uses silicone to seal the face in patient interface cushions, fabric is more breathable and has the added advantage of being moisture-wicking and sweat-absorbent. It can also absorb some oils, making the wearer feel more refreshed and preventing skin sensitivity issues. Fabric also reduces the likelihood that the cushion will shift due to sweat or oils, a common issue with silicone. Additionally, fabric is more skin-friendly than silicone, enhancing the user's comfort and reducing the discomfort felt while undergoing treatment. This helps alleviate the user's mental state and results in better compliance. Moreover, the inclusion of the fabric reduces contact between the cushion's elastic part and the user's face, thereby extending the cushion's lifespan.
3. Compared to existing silicone patient interface cushions, various embodiments as discussed herein use a fabric component that offers particular advantages for certain user groups, such as those with beards or facial indentations due to injuries. The softer fabric can fill in gaps and contours, like the small protrusions formed by facial hair. In contrast, with one-piece elastic components, gaps can form around the beard area when the elastic component is in contact with the face, reducing the sealing performance of the patient interface cushion. The softer fabric is more adaptable to the facial contours and, under the pressure of the face, can fill in the gaps around the beard area to achieve better sealing.
4. Compared to existing technologies for mask liners or cushions, the patient interface cushion of the various embodiments as discussed herein combines the advantages of both the fabric part and the elastic part while also securing the fabric part to the elastic part. This ensures that the curvature of the second surface of the fabric part conforms to the curvature of the outer surface of the elastic part, enabling better fit to the contours of the human face. The fixed attachment between the fabric and elastic parts prevents the fabric from wrinkling due to head movement or facial muscle changes during sleep, which could otherwise lead to air leakage and decreased treatment effectiveness. Since the fabric part is attached to the elastic part as part of the overall patient interface cushion, the steps for use are simplified. There's no need for the tedious adjustment of mask liners or cushions, making it more convenient for the user.
5. Compared to existing foam interface cushions, the manufacturing process of this disclosure is simpler, as this interface cushion has a lower defect rate, and is more cost-effective. The research and production processes for foam interface cushions are challenging and involve foreseeable difficulties with foam materials, foam shapes, and the bonding of foam material with silicone. First, the choice of foam material is critical. It requires finding the right softness and firmness through various ratio tests to ensure that the foam's permeability does not affect treatment effectiveness. Additionally, a new silicone material must be developed to support the foam part, followed by a series of tests to determine the foam's height, shape, and contour in relation to the silicone part. Secondly, in terms of production, the molding and manufacturing cycles for foam materials are longer compared to plastics and silicones. The general production process for foam involves creating a cube through a foaming process, dividing it into suitable thickness, shaping it through cutting or molding, and then joining it with the silicone part. Each step is challenging, and a mistake in one step can impact subsequent production steps. In contrast, this disclosure utilizes common, comfortable fabrics found in everyday life. The desired shape can be achieved simply by cutting the fabric, which is then attached to the elastic part to complete the molding process. Compared to foam interface cushions, this disclosure simplifies the production process, saving on research and production costs. Fewer manufacturing steps also mean a lower likelihood of errors and, consequently, a lower defect rate for the product.

The various technical features described in the above embodiments can be combined in any manner. To keep the description concise, not all possible combinations of these technical features have been described. However, as long as these combinations do not contradict each other, they should be considered within the scope of this specification.

The embodiments described above represent only a few ways in which the disclosure can be implemented. They are specific and detailed, but should not be interpreted as limiting the scope of the patent for the disclosure. It should be noted that those skilled in the art can make various modifications and improvements without departing from the concept of this disclosure, and these fall within the protection scope of this disclosure. Therefore, the scope of protection for this disclosure should be determined by the appended claims.

The invention claimed is:

1. A patient interface cushion with a fabric part, for delivering pressurized breathing gas to a user's nasal and oral airways, the patient interface cushion with the fabric part comprising:
   a rigid part configured to provide support to an elastic part, one end of the rigid part having a first opening configured to receive breathing gas from a continuous positive airway pressure (CPAP) device, and an other end featuring a second opening that communicates with an inner cavity of the elastic part;
   the elastic part configured to connect with the rigid part and provide an attachment surface for the fabric part, having a third opening adjacent to the rigid part that communicates with the second opening, and a fourth opening away from the rigid part configured to allow a user's mouth and a user's nose to enter the inner cavity of the elastic part; and
   the fabric part configured to enclose the user's nose and the user's mouth by forming a sealing area between a lower lip area and a nasal bridge area, having a first surface that adheres to and is partially connected to an outer surface of the elastic part, and a second surface away from the elastic part for sealing at least a portion of the nasal bridge area;
   wherein the fabric part consists of an inner edge adjacent to the fourth opening and an outer edge away from the fourth opening, the inner edge being smaller than or equal to the fourth opening of the elastic part, and the inner edge of the fabric part also including a hanging portion, wherein the hanging portion is configured to be blown up under action of the pressurized breathing gas for sealing around a face of the user,
   wherein a thickness of the fabric part is between 0.6 mm and 3.5 mm, and
   wherein distances of displacements at different points on the second surface of the fabric part vary when a same level of pressure is applied to the different points on the fabric part in an X-axis direction.

2. The patient interface cushion with the fabric part according to claim 1, wherein the rigid part is made of a first material, the elastic part is made of a second material, and the fabric part is made of textile material, the first material being polycarbonate, and the second material being silicone with a hardness at or between 30 A to 70 A on a Shore scale.

3. The patient interface cushion with the fabric part according to claim 2, wherein a material of the fabric part is a combination of one or more of the following: cotton fibers, linen, polyester fibers, elastane fibers, nylon fibers, acrylic fibers, rayon fibers, and spandex fibers.

4. The patient interface cushion with the fabric part according to claim 1, wherein the first surface of the fabric part and the outer surface of the elastic part are directly connected and non-detachable by being directly connected by at least one of silicone adhesive, heat pressing, or molding.

5. The patient interface cushion with the fabric part according to claim 1, wherein the outer edge of the fabric part is larger than an outermost annular projection of the elastic part in an X-axis direction.

6. A patient interface cushion with a fabric part, for delivering pressurized breathing gas to a user's nasal and oral airways, the patient interface cushion with the fabric part comprising:
   a rigid part configured to provide support to an elastic part, one end of the rigid part having a first opening configured to receive breathing gas from a continuous positive airway pressure (CPAP) device, and an other end featuring a second opening that communicates with an inner cavity of the elastic part;
   the elastic part configured to connect with the rigid part and provide an attachment surface for a fabric part, having a third opening adjacent to the rigid part that communicates with the second opening, and a fourth opening away from the rigid part configured to allow a user's mouth and a user's nose to enter the inner cavity of the elastic part;
   the fabric part configured to form a sealing area between a lower lip area and a nasal bridge area, having a first surface that is adjacent to an outer surface of the elastic part, a second surface away from the elastic part for sealing at least a portion of a face of the user, an inner edge adjacent to the fourth opening, and an outer edge away from the fourth opening; and
   an adhesive layer positioned between the outer surface of the elastic part and the first surface of the fabric part, that connects the elastic part and the fabric part;
   wherein the elastic part further comprises protruding pieces on a lateral nasal area for fitting against nasal sidewalls, and the inner edge of the fabric part is larger than the fourth opening of the elastic part, both the elastic part and the fabric part being configured to jointly contact the face of the user wherein the elastic part contacts the nasal sidewalls and the fabric part contacts a face of the user for sealing the face of the user; and
   wherein the fabric part has a degree of elasticity and adapts to a curvature change of the elastic part when subjected to pressure, and distances of displacements at different points on the second surface of the fabric part vary when a same level of pressure is applied to different points on the fabric part in an X-axis direction.

7. The patient interface cushion with the fabric part according to claim 6, wherein the adhesive layer comprises a glue or double-sided tape layer, with a thickness at or between 0.01 to 0.3 mm.

8. The patient interface cushion with the fabric part according to claim 6, wherein a surface area of the second surface of the fabric part is at least 3.5% of an outer surface area of the elastic part.

9. The patient interface cushion with the fabric part according to claim 6, wherein the fabric part is single-layered and has a uniform thickness.

10. The patient interface cushion with the fabric part according to claim 6, wherein the fabric part is cut into an approximately annular outline using laser, die-cutting, or ultrasonic methods, and a shape of the inner edge is triangular or teardrop-shaped.

11. A patient interface cushion with a fabric part for delivering pressurized breathing gas to a user's nasal and oral airways, the patient interface cushion with the fabric part comprising:
   a rigid part configured to provide support to an elastic part, one end of the rigid part having a first opening configured to receive breathing gas from a continuous positive airway pressure (CPAP) device, and an other end featuring a second opening that communicates with an inner cavity of the elastic part;
   the elastic part configured to connect with the rigid part and provide an attachment surface for a fabric part, having a third opening adjacent to the rigid part that communicates with the second opening, and a fourth opening away from the rigid part configured to allow a user's mouth and a user's nose to enter the inner cavity of the elastic part;
   the fabric part configured to enclose the user's mouth and the user's nose by forming a sealing area between a lower lip area and a nasal bridge area, having a first surface that is adjacent to an outer surface of the elastic part, a second surface away from the elastic part that seals at least a portion of a face of the user, an inner edge of the fabric part being adjacent to the fourth opening and larger than the fourth opening such that both the elastic part and the fabric part are configured to jointly contact the face of the user along a connection between the inner edge and the elastic part of the fourth opening, and an outer edge away from the fourth opening;
   wherein the fabric part has one or more of the following characteristics:
   a surface area of the second surface being at least 3.5% of the outer surface area of the elastic part;
   a water absorption time less than 30 seconds, according to a AATCC 79 test method; and
   a surface roughness of the second surface having a Ra value at or between 0.2 to 10 microns.

12. The patient interface cushion with the fabric part according to claim 11, wherein the fabric part has an air permeability rate of 0.5-30 ftv/ft$^2$/min when tested according to a ASTM D737 test method.

13. The patient interface cushion with the fabric part according to claim 11, wherein a material of the fabric part is a combination of one or more of the following: cotton fibers, linen, polyester fibers, elastane fibers, nylon fibers, acrylic fibers, rayon fibers, and spandex fibers.

14. The patient interface cushion with the fabric part according to claim 11, wherein a diameter of the first opening is at or between 10 to 45 mm, the first opening is smaller than the second opening.

15. A patient interface cushion with a fabric part for delivering pressurized breathing gas to a user's nasal and oral airways, the patient interface cushion with the fabric part comprising:
   a rigid part configured to provide support to an elastic part, one end of the rigid part having a first opening configured to receive breathing gas from a continuous positive airway pressure (CPAP) device, and an other end featuring a second opening that communicates with an inner cavity of the elastic part;
   the elastic part configured to connect with the rigid part and provide an attachment surface for the fabric part, having a third opening adjacent to the rigid part that communicates with the second opening, and a fourth opening away from the rigid part configured to allow a user's mouth and a user's nose to enter the inner cavity of the elastic part;
   the fabric part configured to form a sealing area between a lower lip area and a nasal bridge area, having a first surface that is adjacent to an outer surface of the elastic part, and a second surface away from the elastic part for sealing at least a portion of the nasal bridge area, an inner edge of the fabric part being adjacent to the fourth opening and larger than the fourth opening such that both the elastic part and the fabric part are configured to jointly contact the face of the user along a connection between the inner edge and the elastic part of the fourth opening, and an outer edge away from the fourth opening; and
   an adhesive layer positioned between the outer surface of the elastic part and the first surface of the fabric part that connects the elastic part and the fabric part;
   wherein a connection between the elastic part and the fabric part via the adhesive layer is configured to be removably attachable and detachable, and an adhesive force provided by the adhesive layer to the fabric part is greater than a weight of the fabric part.

16. The patient interface cushion with the fabric part according to claim 15, wherein a thickness of the fabric part is at least 0.6 mm and at most 3.5 mm.

17. The patient interface cushion with the fabric part according to claim 15, wherein a width of the fabric part is at least 10 mm.

18. The patient interface cushion with the fabric part according to claim 15, wherein the fabric part is only provided on portions of the elastic part.

19. The patient interface cushion with the fabric part according to claim 15, wherein a connection between the elastic part and the fabric part via the adhesive layer is detachable, and the adhesive layer is made of peelable adhesive or double-sided tape.

20. The patient interface cushion with the fabric part according to claim 15, wherein the fabric part is multi-layered, and a layer adjacent to the elastic part is made of a low-permeability material to prevent the adhesive layer from seeping through to the second surface.

* * * * *